(12) United States Patent
Clarke et al.

(10) Patent No.: US 9,340,312 B2
(45) Date of Patent: May 17, 2016

(54) METHOD AND A DEVICE FOR HANDLING SAMPLE CONTAINERS

(71) Applicant: ANDREAS HETTICH GMBH & CO. KG, Tuttlingen (DE)

(72) Inventors: Gavin Clarke, Tuttlingen (DE); Klaus-Guenter Eberle, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 607 days.

(21) Appl. No.: 13/686,020

(22) Filed: Nov. 27, 2012

(65) Prior Publication Data

US 2013/0239527 A1    Sep. 19, 2013

(30) Foreign Application Priority Data

Nov. 30, 2011 (DE) .......................... 10 2011 055 899

(51) Int. Cl.
*B65B 69/00* (2006.01)
*G01N 35/00* (2006.01)
*B01L 3/14* (2006.01)
(Continued)

(52) U.S. Cl.
CPC ............ *B65B 69/00* (2013.01); *B01L 3/50825* (2013.01); *B67B 7/02* (2013.01); *B67B 7/182* (2013.01); *G01N 35/0099* (2013.01);
(Continued)

(58) Field of Classification Search
CPC ............ B65B 69/00; B67B 7/00; B67B 7/02; B67B 7/14; B67B 7/162; B67B 7/164; B67B 7/18; B67B 7/182; G01N 2035/00772; G01N 2035/0405; G01N 2035/041; G01N 2035/0493

USPC ............... 53/492, 75, 76, 381.4; 81/3.4, 3.42, 81/3.44

See application file for complete search history.

(56) References Cited

U.S. PATENT DOCUMENTS 5,080,864 A * 1/1992 Shaw ............................... 422/62
5,490,321 A * 2/1996 Kaneko ........................... 29/714
(Continued)

FOREIGN PATENT DOCUMENTS

DE        19911351 A1    9/2000
EP         1157965 A1   11/2001
(Continued)

OTHER PUBLICATIONS

EPO machine translation of DE 19911351, retrieved from espacenet.com, Jun. 26, 2105, 12 pages.*

(Continued)

*Primary Examiner* — Stephen F Gerrity
(74) *Attorney, Agent, or Firm* — Woodling, Krost and Rust

(57) ABSTRACT

The invention relates to a method for automatically handling a sample container (100), wherein at least one sample container (100) is taken up in a container carrier (30) in a handling device (95) and a lid (101) is gripped by a gripper head (50) with a predetermined gripping force and the lid (101) is removed by a combined movement out of a translational and rotational movement from the sample container (100). Using an optical capturing device, the lid (101) as well as the sample container (100) are analyzed and are assigned to a lid and sample container type, and that, furthermore, a required torque is assigned to each lid and/or sample container type as required for removing the lid (101), and that, starting from the required torque, the gripping force of the gripper head (50) is adjusted.

9 Claims, 5 Drawing Sheets

(51) Int. Cl.
   *B67B 3/02* (2006.01)
   *B67B 7/18* (2006.01)
   *B67B 7/02* (2006.01)
   *B01L 3/00* (2006.01)
   *G01N 35/10* (2006.01)
   *G01N 35/04* (2006.01)

(52) U.S. Cl.
   CPC . *G01N 35/1079* (2013.01); *G01N 2035/00772* (2013.01); *G01N 2035/041* (2013.01); *G01N 2035/0405* (2013.01)

(56) References Cited

U.S. PATENT DOCUMENTS

| | | | | |
|---|---|---|---|---|
| 5,721,384 | A * | 2/1998 | Tanihata | 73/864.81 |
| 6,871,566 | B2 * | 3/2005 | Niwayama et al. | 81/3.2 |
| 7,141,213 | B1 * | 11/2006 | Pang et al. | 422/65 |
| 8,859,289 | B2 * | 10/2014 | Marty et al. | 436/48 |
| 2001/0019701 | A1 * | 9/2001 | Braun et al. | 422/63 |
| 2005/0163354 | A1 * | 7/2005 | Ziegler | 382/128 |
| 2005/0210671 | A1 * | 9/2005 | Itoh | 29/801 |
| 2008/0047369 | A1 * | 2/2008 | Tsujimura et al. | 73/863.01 |
| 2009/0035185 | A1 * | 2/2009 | Tsujimura et al. | 422/99 |
| 2010/0261595 | A1 * | 10/2010 | Schaefer et al. | 494/20 |
| 2011/0085951 | A1 * | 4/2011 | Nakahana et al. | 422/549 |
| 2012/0134769 | A1 * | 5/2012 | Friedman et al. | 414/751.1 |
| 2013/0136569 | A1 * | 5/2013 | Rosmarin et al. | 414/618 |

FOREIGN PATENT DOCUMENTS

| | | |
|---|---|---|
| EP | 2282212 A1 | 2/2011 |
| JP | 2000-81441 | 3/2000 |
| JP | 2003-94374 | 4/2003 |
| JP | 2007-85967 | 4/2007 |
| WO | 2009141957 A1 | 11/2009 |

OTHER PUBLICATIONS

German Patent and Trademark Office, Office Action, May 30, 2012, German Application No. 102011055899.3, Applicant Andreas Hettich GmbH & Co. KG, Munich Germany, pp. 1-6.

Japan Patent Office, Notification of Reason for Refusal, English Translation of Office Action, Japanese Patent Application No. 2012-260179, Nov. 26, 2013, pp. 1-5, Japan.

Japan Patent Office, Notification of Reason for Refusal, Office Action, Japanese Patent Application No. 2012-260179, Nov. 26, 2013, pp. 1-7, Japan.

* cited by examiner

METHOD AND A DEVICE FOR HANDLING SAMPLE CONTAINERS

This application claims the foreign priority benefit under Title 35, United States Code, §119 (a)-(d) of German Patent Application No. DE 10 2011 055 899.3, filed on Nov. 30, 2011 in the German Patent Office, the disclosure of which is herein incorporated by reference in its entirety.

The invention relates to a method for handling sample containers and a device for handling sample containers.

Sample containers are used for storing of samples to be analyzed. In the course of a preparation process for the analysis, the sample containers filled with the respective samples, have to be handled by handling devices in many different ways.

Therein, the sample containers usually must be positioned in predetermined, closely restricted positions for handling thereof. However, it happens once and again that the sample containers do not keep the close limits of the predetermined positions and, thereby, cannot be handled in the desired manner.

This impairs the functional safety of the handling devices to a substantive extent, in particular of cover removing devices.

Since cover removing devices are integrated into higher ranking processes in many cases, they have a central importance resulting in a high level of a required functional safety.

The EP 2 282 212 A1 discloses a cover removing device. According to this publication, for removing a lid, a gripper head is put to a lid of the sample container, wherein the lid is removed from the container by a combined movement out of a translational and rotational movement. By means of this kind of lid removal, screw cap lids as well as press-lock lids may be removed from a container with one device.

However, this device has the deficiency that the gripping ranges of the gripper head have to be manually adapted for adaption to different kinds of lids. Furthermore, an oblique position of the sample container cannot be tolerated.

The invention is based on the object to provide a method and a device for handling of sample containers which comprise an improved functional safety and which have a larger flexibility in the automatic handling of differing sample containers and types of lids.

In a manner known per se, at least one sample container is taken up in a container carrier in a handling device for the automatic cover removal from a sample container. The lid of a sample container is gripped by a gripper head with a predetermined gripping force. The lid is removed from the sample container by a combined movement out of translational and rotational movement.

According to the invention, the method is characterized in that the lid as well as the sample container are analyzed by an optical detection device, and are assigned to a defined type of lid and sample container. Furthermore, a torque required for removing the lid is assigned to each type of lid and/or sample container. Starting from this torque, the gripping force of the gripper head is adjusted.

By adapting the gripping force to different types of lid and sample containers, a plurality of different types of lids and types of sample containers may be processed without changing the gripping range geometry of the gripper head. Therefore, a safe automatic processing is achieved without manual intervention.

According to a further aspect of the invention, the removal of the lid is carried out thereby that a sample container is gripped in the carrier unit by a lifting gripper and is lifted out of the carrier unit. Subsequently, the gripper head grips the lid where upon the lifting gripper releases the grip on the sample container. Subsequently, the gripper head carries out a rotation of at least 360° with the gripped sample container. After the rotation, the sample container is again gripped by the lifting gripper. Subsequently, the cover is removed from the sample container by a combined movement out of a translational and rotational movement of the gripper head. The sample container is brought back into its starting position in the carrier unit after removal of the lid.

By means of the rotation of the sample container, a sample container which is possibly orientated not absolutely vertical, may brought back into the vertical position. Thereby, a possible canting upon the removal of the lid may be avoided. The reliability and safety against errors can be put up thereby.

In particular, the gripping force of the lifting gripper is adapted to the required torque.

Preferably, after gripping the sample container with the lifting gripper and after the rotation of the sample container, the cover gripping device is opened. After being opened anew, the cover is gripped with a gripping force which is required for providing the required torque in order to remove the lid from the sample container with a combined movement out of a translational and rotational movement.

In a particularly advantageous way, the gripping force correlates with the translational displacement path of the gripper head. The gripping force with which the gripper head grips the lid, is adjusted through the positioning of the gripper head in its vertical position.

In particular, the gripping point of the gripper head on the lid is defined where a corresponding vertical position is approached which corresponds to the gripping force to be applied for the required torque. The position of the lid with respect to the gripper head is approached by means of the lifting gripper and is set thereby.

The vertical position of the gripping position or the height, respectively, into which the sample container is brought, is defined depending on the torque to be applied.

Preferably, during the rotation of the sample container for the vertical positioning thereof, also a code applied to the sample container, in particular a bar code, may be read by a capturing device.

For this purpose, the optical capturing device is, in particular, arranged such that, besides the type of the sample container and the lid, also a code may be read out. By means of the rotation of the container about at least 360°, it can be assured that a code applied to the sample container will be read in any case.

Furthermore, the position of the code or the rotational positioning of the sample container, respectively, may be memorized, and the code may be rotated into a defined position by rotation of the sample container beyond 360°. A defined position may, for example, be given by the position of a viewing window in a carrier unit.

In this way, the synergies between the cover removal and the process control can be used whereby two tasks can be carried out in one working step.

In a further development of the invention, it is envisioned that the position of the sample container in the carrier unit is controlled by an optical system. Therein, in particular a canting, i.e. a positioning deviating from a vertical position of the sample container is evaluated.

The position of the sample container may, at the one hand, be controlled prior to the lid removal where upon, in case of an oblique positioning, a handling of the sample container deviating from the normal handling may be started.

Furthermore, the position of the sample container may be controlled after the lid removal. This has the advantage that a subsequent process depending on the oblique positioning of the sample container may be initiated. For example, a container positioned obliquely beyond the tolerance may be rejected.

According to a further advantageous embodiment of the invention, the color of the lid may be evaluated by a capturing device, wherein a color of the lid of a cover type is correlated to a processing specification. For example, a lid having a predetermined color which lid is not to be opened in any case out of the security reasons or based on an elevated contamination danger for the probes, can leave the handling device without being opened.

For carrying out the method, a device according to the invention for handling of sample containers, in particular for tube shaped sample containers, is provided.

The device for automatic handling of a sample container has a gripper head which is connected to a control unit wherein the gripper head comprises at least two forcipate gripping jaws. The gripper head may be displaced in its vertical position by means of a motor in a combined movement out of a translational vertical and a rotational movement, wherein the opening angle of the gripping jaws is depending on the vertical movement distance of the gripper head.

According to the invention, the handling device comprises an optical capturing device which is connected to the control device. By means of this optical capturing device, a typing of the sample container as well as the lid is possible. By processing the typing, the size of the sample container, the kind of closing the lid as well as the required minimum torque which is required for opening the lid, may be read out.

The gripping force with which the gripper head can grip the lid, is, in particular, provided by springs which connect the gripping jaws. Thereby, the tensioning force of the tensioning jaws depends on the opening angle of the gripper head jaws.

In particular, the gripping range of the gripping jaws is arranged such that it comprises a serration which is preferably directed to the rotational direction. Furthermore, a spring is provided in the gripping range which extends, in its relaxed state, beyond the serration but is pressed away, however, upon a load created on gripping the lid.

By means of the spring, a lid may easily be released again from the gripping jaws after the cover removal process.

The gripping jaws may, furthermore, comprise, in their gripping range, lugs which recline across the sample container during the lid removing process. Thereby, a discharge of the content of the sample container during the cover removal process is avoided.

In a further advantageous embodiment, the optical capturing device is provided with a color recognition feature so that the different cover colors may be differentiated. Depending on the evaluated lid color, subsequent processes may be stored in which, for example, a lid may not be opened in any case out of security reasons or because of an enlarged danger of contamination, where the handling device may be left without cover removal.

According to an embodiment of the invention, the optical capturing device may be arranged such that the respective rotational positioning of the sample container in the sample container carrier can be recognized. Furthermore, the optical capturing device is able to read a code which is provided at the circumferential walls of the respective sample containers as well as to transmit to the control device the detected rotational positioning and the read-out codes.

In this way, besides the application and/or removal of the lid, additional information on the sample container and/or the sample contained therein may be read into the system simultaneously.

According to a further embodiment of the invention, the optical capturing device is arranged to detect a cover removed state and a cover applied state of the respective sample container and to transmit this to the control device.

Thereby, it may be determined, at the one hand, whether the intended cover removal or cover application operation was successful or not and, on the other hand, a malfunction of the device (for example by attempting cover removal of a coverless sample container) may be avoided.

Accordingly, according to an embodiment of the invention, the gripper head is controllable by the controller device in case the lid of the respective sample container is to be removed, in order to allow the lid removal for this sample container based on a cover removed state prior to a cover removal operation of the handling device.

According to a further aspect of the invention, the device for automatic handling of a sample container may comprise a gripper head which is connected to a control device wherein the gripper head comprises at least two forcipate gripping jaws. The gripper head is movable in its vertical position by means of a motor in a combined movement out of a translational, vertical and rotational movement, wherein the opening angle of the gripper head jaws may depend on the vertical movement distance of the gripper head. Besides of the gripper head, a lifting gripper may be provided which is connected to the control device wherein the lifting gripper comprises a gripping range for determining the sample container, and the lifting gripper is connected to a motor such that it can elevate the sample container, hold it and put it down.

The lifting gripper comprises in particular two legs at the ends of which a gripping area each is arranged. The drive of the legs of the lifting gripper is affected by a rotating disc which comprises an eccentric guiding path within which the free ends distant from the gripping area are guided. The rotation of the rotating disc has the result of a change of distance between the two free ends distant to the gripping area. This again leads to a gripping movement at the end of the gripping range based on the support in the central area of the legs.

The gripping range of the lifting gripper is arranged such that it may take up different sample diameters, in particular of circular cross section. This is achieved, in particular, by two springy, crossing jaws. The gripping area is formed, furthermore, by formations at the gripper end of the legs of the lifting gripper, and it may comprise an engagement surface having an elliptical basic shape.

Therefore, according to the invention, tube-like sample containers having a diameter from 11 to 16.5 mm may be handled.

Preferably, a vertical movement of the gripper head may be affected by a rotational movement of the gripper head with respect to a threaded shaft. Thereby, a translational and a rotational movement can be generated with only one motor.

The shaft is rotated up into an end position in which a stop is provided. At the stop position, the gripper jaws comprise a maximum opening angle for gripping a lid. In case the motor rotates beyond this range, a lid is released in each case. Preferably, this is the case at a rotation of 120° beyond the stop.

According to further embodiment of the invention, the gripper head is to be controlled by the control device in order to rotationally adjust, based on the known rotational positioning of the sample containers, them in the sample container carrier such that the respective codes of the sample containers are visible through inspection recesses provided each at the side of the sample container carrier.

Thereby, it is advantageously ensured that the codes of the respective sample containers can be read out reliably during subsequent operations without having to take out the sample containers of the sample container carrier.

Therefore, sample containers and lids of different types may be handled with the inventive device in a variable way.

According to a further embodiment of the invention, the optical capturing device comprises a camera which is arranged at the capturing station.

Furthermore, a second optical capturing device may be provided for determining the positioning of a sample container. It is arranged opposite to a mirror surface. The mirror surface and the second optical capturing device are located, during the determination of the position, in a plane with a vertical target position of the sample container inserted into the container carrier.

According to a further aspect of the invention, the gripper head comprises a flexible support.

By means of the flexible support of the gripper head and the possibility to balance oblique positions of the sample containers, the limits for the predetermined positioning (vertical positioning here) of the sample containers which are predefined for a safe handling, can be extended. Thereby, such limits can, as a rule, be kept during the operation of the device so that the sample containers can be handled in the desired way and no malfunctions are occurring. Thereby, the inventive device has an improved functional safety.

According to a further embodiment of the invention, the device comprises an unloading station for unloading the sample container carriers carrying the sample containers, wherein the optical capturing device comprises a camera which is arranged at the unloading station.

According to an embodiment of the invention, the camera arranged at the unloading station is arranged to determine for each of the sample containers taken up in the sample container carrier a malfunction and to transmit this to the control device.

The invention extends explicitly also to such embodiments which are not defined by combinations of features out of explicit back referencing of the claims, where the disclosed features of the invention, as far as this makes technically sense, may be combined with each other in an arbitrary way.

Further advantages, features and potential applications of the present invention may be gathered from the description which follows, in conjunction with the embodiments illustrated in the drawings.

Throughout the description, the claims and the drawings, those terms and associated reference signs will be used as are notable from the enclosed list of reference signs.

In the following, a device for handling of sample containers of an embodiment of the invention is described with reference to the FIGS. 1 to 7.

Figure 1:
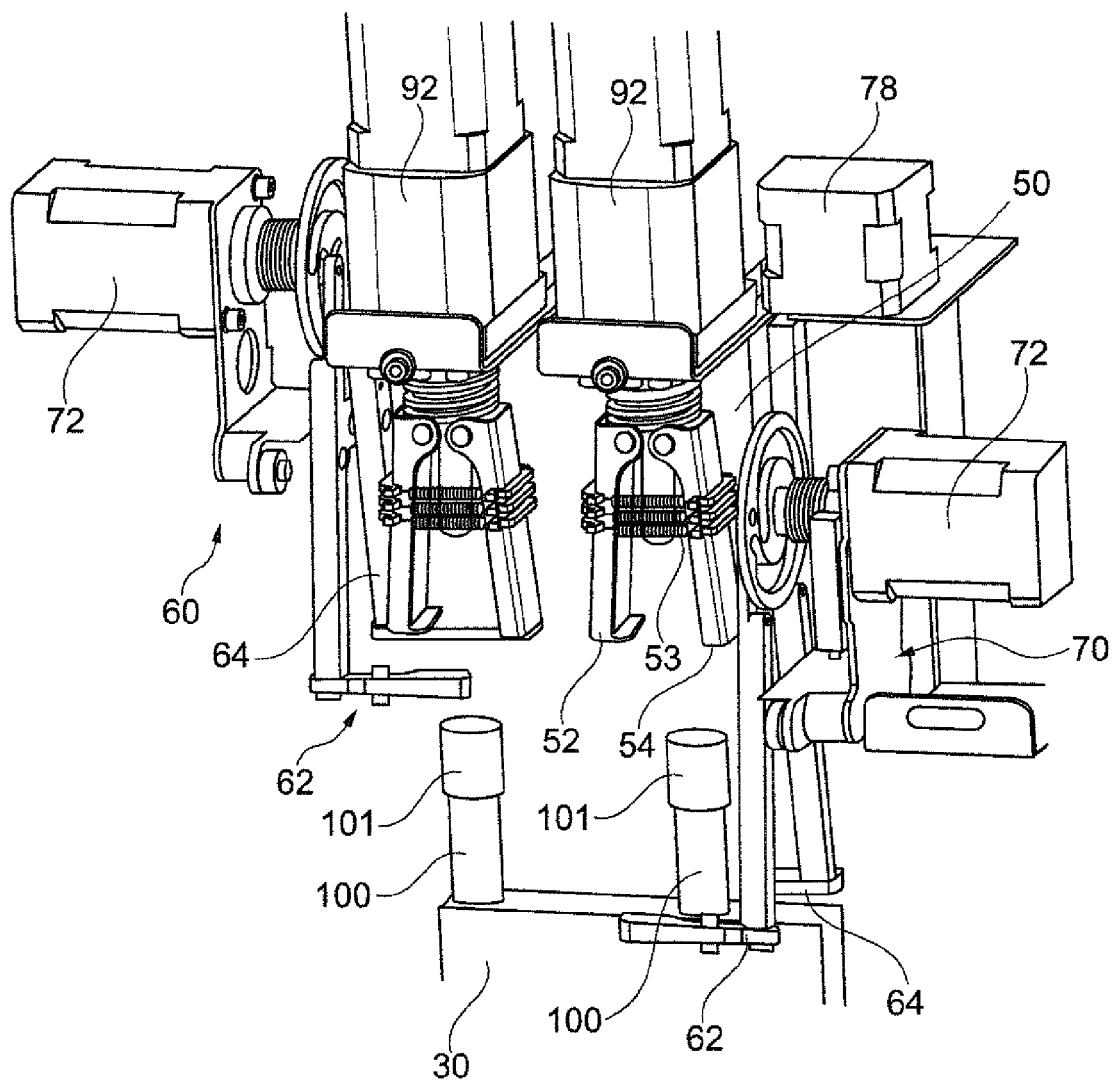
FIG. 1 shows a part of an inventive handling device having two processing stations.

FIG. 1 shows a part of the handling device 95 of the invention having two processing stations. One processing station comprises a lifting gripper 60 which can carry out a gripping function by means of a motor 72, wherein the legs 62, 64 are positioned around a sample container 100. Subsequently, the gripped sample container 100 can be vertically moved by means of the motor 78. In this way, the sample container 100 can be removed from a carrier unit 30 and supplied to the gripper head 50. The gripper head 50 applies a gripping force to the lid 101 of the sample container which force results from the adjustment of the springs connecting the gripping jaws 52, 54.

Figure 2:
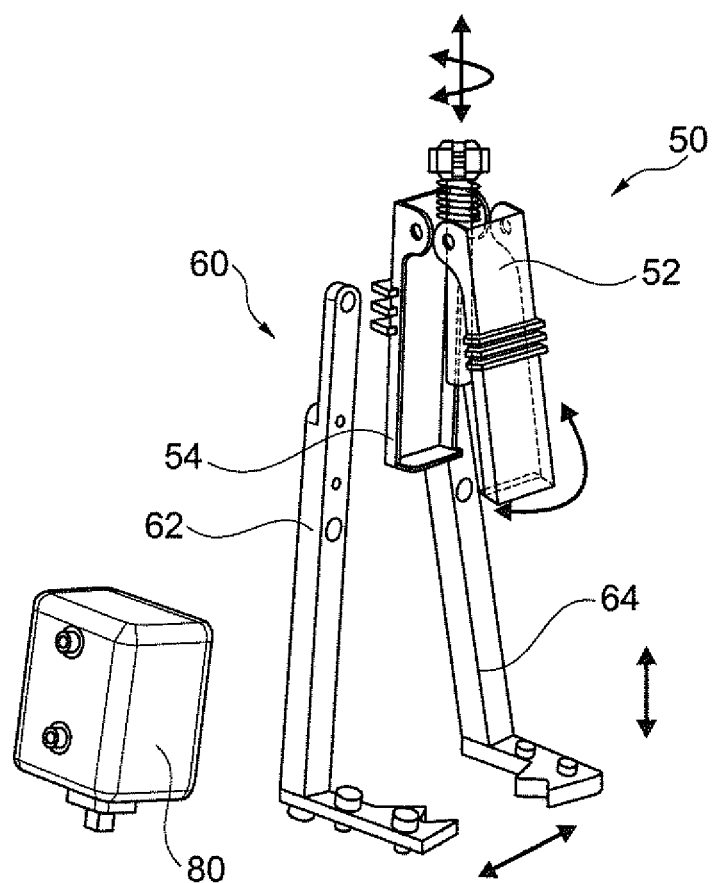
FIG. 2 shows the essential components of the handling device of the invention.

FIG. 2 shows the essential components of the handling device of the invention in a perspective view. The handling device comprises a gripper head 50, a lifting gripper 60 as well as a camera 80. The drive means driving the gripping devices 50, 60 are not shown for simplifying this Figure. The camera 80 is arranged such that it can capture a supplied sample container. The camera 80 is embodied as an intelligent camera and it can determine the type of sample container as well as the type of lid based on the picture of the sample container. For this purpose, the camera processes the shape and the surface of the sample container and the lid.

According to the result of the determination, the sample container as gripped by the lifting gripping device 60 is displaced in its height. The information related to the type of lid is processed such that, by means of the control device (not shown), a position is communicated to the gripper head 50 into which it has to be moved in order to ensure a sufficient opening angle of the gripping jaws 52, 54 so that the sample container may be inserted there between. When the sample container is positioned accordingly, the jaws 52, 54 may be closed by the spring force applied through the springs 53 by means of the rotational movement of the motor (not shown) driving the gripper head 50.

When the sample container is gripped by the gripper head, the legs 62, 64 are pivoted to the outside and release, thereby, the gripped sample container. The sample container is now freely held by the gripper head 50. The sample container may be rotated by means of the gripper head 50. During this rotation about at least 360°, a code applied to the sample container, in particular a bar code, may be read by the camera 80. Furthermore, an adjustment of the sample container axially to the rotational axis of the gripper head 50 is affected which ensures that the sample container is vertically adjusted after the rotation. The free rotation of the sample container is finished when a predetermined position for the code or a corresponding rotational positioning of the sample container, respectively, is reached.

When the position is reached, the container is again gripped by the gripping arms 62, 64 of the lifting gripping device 60. After the lifting gripper 60 holds the sample container, a lid of the sample container which is held by the gripper head 50, can be removed by a movement of the gripper head 50 which is composed out of a translational and a rotational movement.

After the lid has been removed, the lid-less sample container is put down through a purely translational movement of the lifting gripper 60 again in the container carrier, and the grip is released by tilting the lifting gripper arms 62, 64. The lid is released by means of again opening the gripper head 50 and is discarded.

Figure 3:
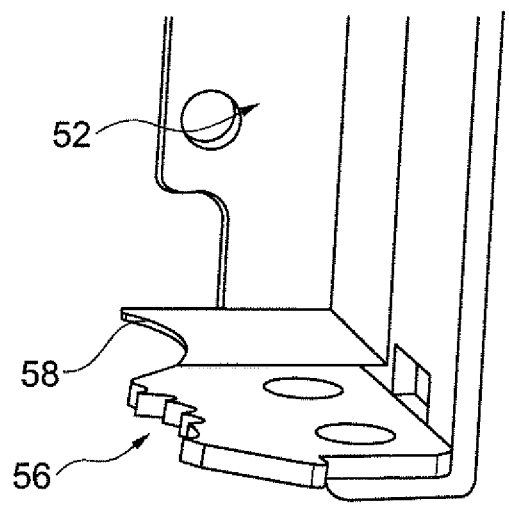
FIG. 3 shows the gripping area of a gripper head leg as a detail.

FIG. 3 shows a part of the gripping area of a gripping jaw 52. The gripping area comprises a serration 56 which is directed in the direction of rotation. Furthermore, a spring 58 is provided which extends beyond the serration in its released state. As soon as the gripper head grips the lid, the spring 58 is forced out of the gripping area. This serves the purpose that, as soon as the gripper head grips the lid, the spring 58 is forced out of the gripping area. This serves the purpose that, after the lid has been taken off the sample container, it does not stick to the serration after opening but is pressed away from the gripping end by the spring. This ensures a reliable loosening of the lid from the gripper head 50.

Figure 4:
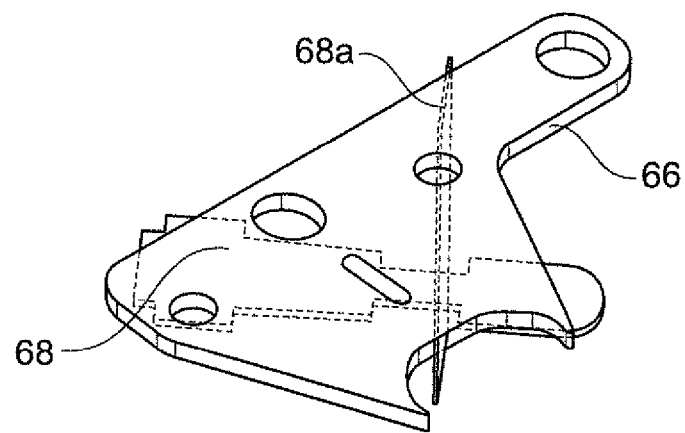
FIG. 4 shows the end area of a leg of the lifting gripper as a detail.

FIG. 4 shows a part of the end area of a leg 62 of the lifting gripper 60. A lower plate 66 is shown which is fixed to the lower leg 62. The upper plate closing of the upper end is not shown out of clarity reasons. The gripping area of the lifting gripping device 60 is correspondingly arranged such that two crossing spring elements 68, 68a form a gripping area. Thereby, it is ensured that independent of any diameter, always a sufficiently large force can be applied to the sample container. The spring elements 68 and 68a are, for this purpose, connected at one end in a torque proof way to the upper and lower plate of the gripping area. Only a sample container diameter gripable at maximum is predefined by the geometry of the plate 66.

Figure 5:
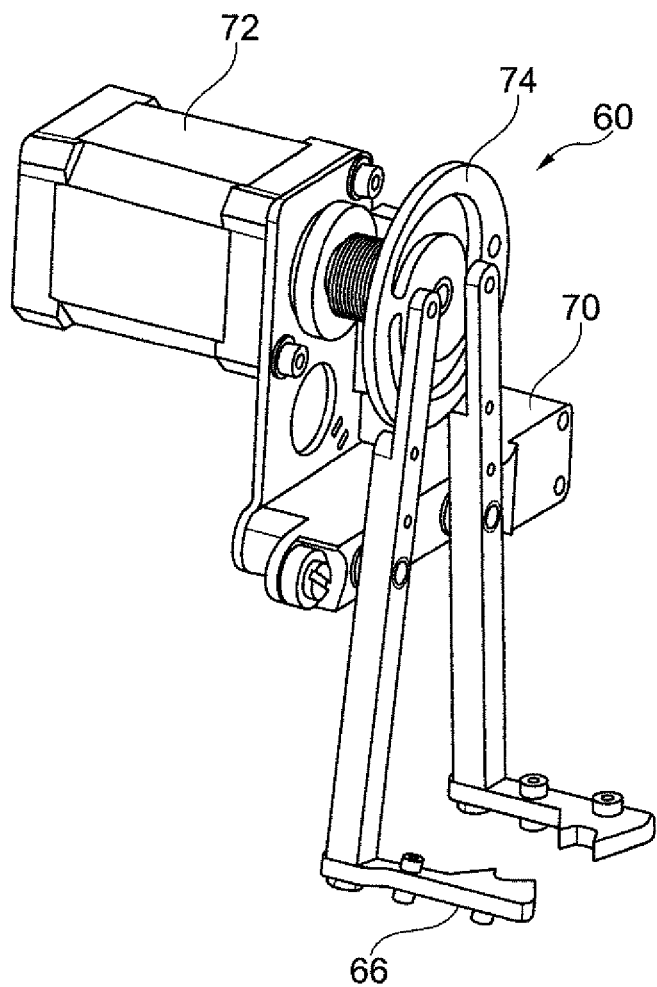
FIG. 5 shows a lifting gripper with its gripping motor.

FIG. 5 shows a lifting gripping device 60 with its motor for the gripping function. The moving device for a vertical movement of the lifting gripper is not shown for clarity reasons of the drawing. The lifting gripper 60 comprises the lifting gripper arms 62 and 64 which end in the gripping area of the lifting gripper 60. The legs 62, 64 of the lifting gripper are rotatably supported in a leg receiving means 70. At the end remote from the gripping area, the legs 62, 64 comprise connection means which are guided in a rotating disc 74 driven by the motor 72. The guiding means is embodied as an eccentric guiding path. Thereby, a rotational movement of the rotor is converted into a lateral movement of the two free ends with respect to each other. Thereby, the gripper is moved to the sample container and moved away therefrom, respectively. The total construction shown is vertically movable by means of the movement means not shown, and is, therefore, adapted to remove a sample container from the carrier unit and to put it back there into. Furthermore, the position of the sample container during the removal of the lid can be defined in this way.

Figure 6:
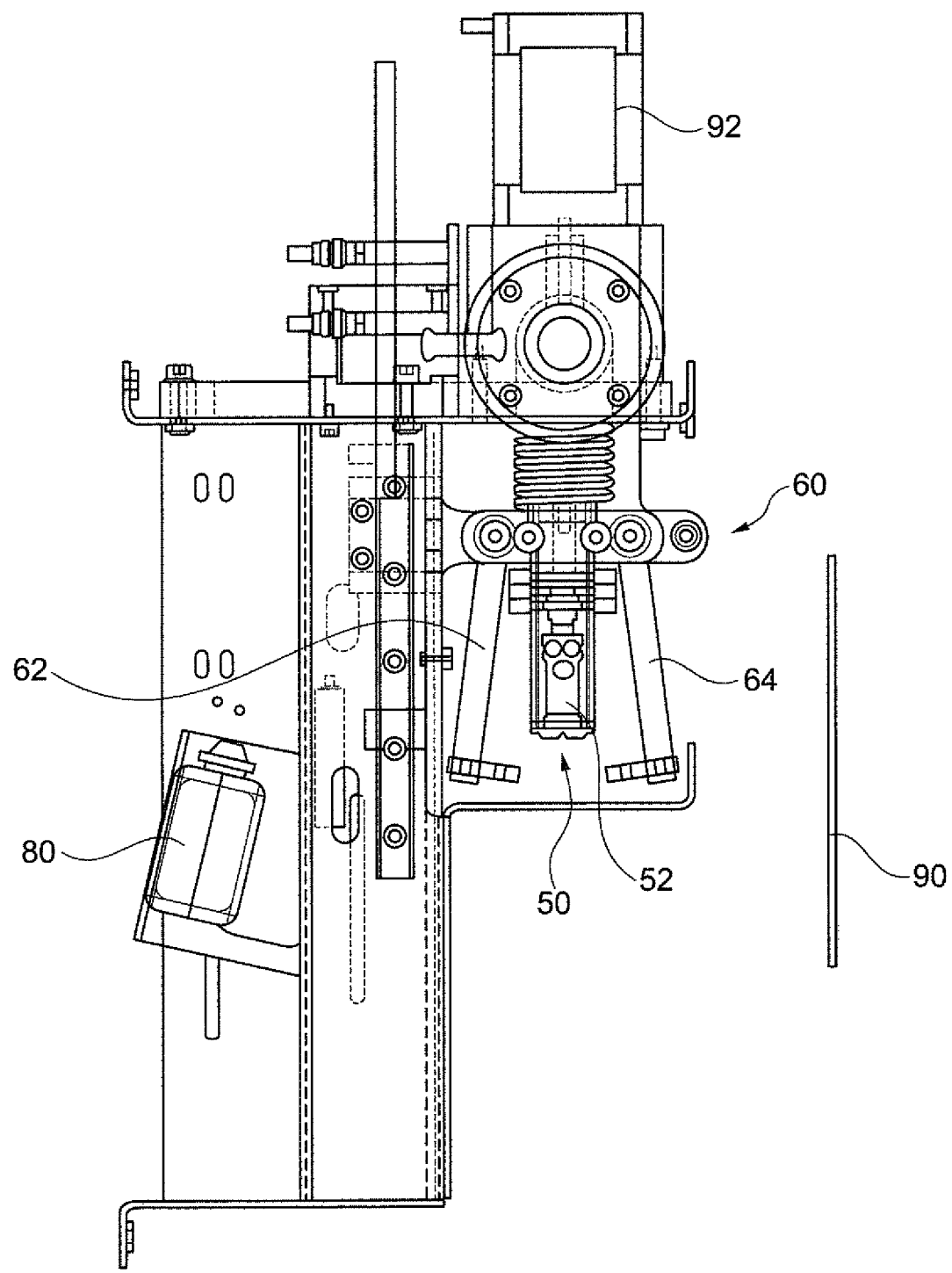
FIG. 6 shows a schematic side view of the handling device.

FIG. 6 shows a schematic side view of the handling device with the lifting gripper 60, the gripper head 50 and the camera 80. Furthermore, also a step motor 92 driving the gripper head 50 is shown. The camera 80 is usable in such a way that it forms an optical system with a mirror juxtaposed thereto. By means of this optical system, an oblique positioning of a sample container can be detected.

Figure 7:
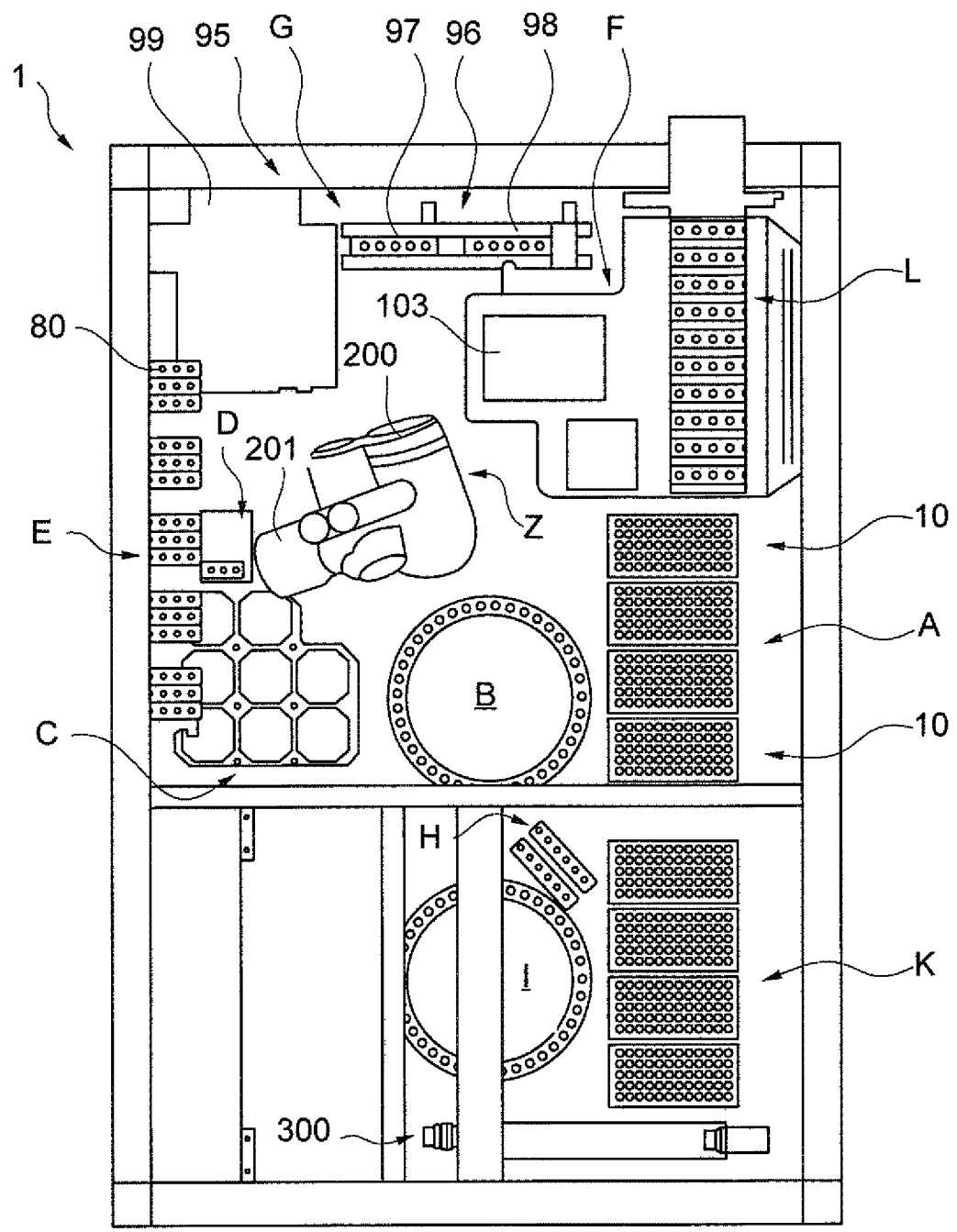
FIG. 7 shows a top view of the sample processing system according to an embodiment of the invention.

FIG. 7 shows a sample processing system 1. It comprises an input storage area A, a first intermediate storage area B, a second intermediate storage area C, a third intermediate storage area D, a fourth intermediate storage area E, a centrifuge area F, a lid removing area G, a fifth intermediate storage area H, a sixth intermediate storage area I and an output storage area K.

About in the middle between the input storage area A, the first intermediate storage area B, the second intermediate storage area C, the third intermediate storage area D, the fourth intermediate storage area E, the centrifuge area F and the lid removing area G, a first robot 200 operating with a linked robot arm is arranged in the central area 10.

Above the fifths intermediate stare H, the sixth intermediate storage area I and the output storage area K, a robot 30 is provided operating like a gantry crane.

In the input storage area A, a plurality of take up module arrangements 10 composed of a plurality of take up modules 11 for taking up sample containers 100 having predetermined dimensions, are arranged and filled with sample containers 100.

The sample containers 100 are preferably formed tube like each like a test tube.

The handling device is also arranged in the housing 99 and comprises at least one gripper head which is, in the course of a movement function, rotating function and gripping function, controllable by a control device (not shown) connected thereto in order to apply the respective lids 101 to the respective open ends of sample containers 100 and/or remove them therefrom.

According to the invention, the gripper head is also flexibly supported so that it can balance an oblique positioning deviating from the vertical positioning of the sample container 100 taken up in the sample container carrier 30.

The device 95 furthermore comprises an optical capturing device (not shown) which is connected to the control device and is arranged to detect the respective rotational positioning of the sample container 100 in the sample container carrier 30 and to read the codes (here for example bar codes) provided on the respective circumferential walls of the sample container 50 and to transmit the detected rotational positioning and the read codes to the control device.

The optical capturing device is, furthermore, configured to detect a lid removed state and a lid applied state of the respective sample container 100 and to transmit this to the control device.

The optical capturing device is further configured to detect the type of sample container and the type of lid and to transmit this to the control device.

The gripper head is controllable from the control device, in order to rotationally adjust, based on the detected rotational positioning of the sample containers 50, them in the sample container carrier 30 such that the respective codes of the sample containers 100 are visible through inspection recesses 83 provided each to the side in the sample container carrier 30.

Furthermore, the gripper head is controllable by the control device to allow, when the lid of the respective sample container is to be removed, based on a lid removed state of a sample container 100 as detected by a lid removal operation of the handling device, for removing the lid of this sample container 100.

Furthermore, the gripper head is controllable by the control device to screw on and off the respective lid as required through a screwing-type rotational movement or to put them on or take them off by a linear movement. The optical capturing device comprises a camera which is arranged at the take up station and a camera which is arranged at the unloading station.

The camera arranged at the unloading station is configured to determine, for each sample container 100 taken up in the sample container carrier 30, a malfunction and to transmit this to the control device.

LIST OF REFERENCE SIGNS

1 sample processing system
10 take up module arrangement
30 sample container carrier
40 carrier unit
50 gripper head
52 gripper jaw
54 gripper jaw
56 serration
58 spring 60 lifting gripper
62 arm
64 arm
66 plate
68 spring element
68a spring element
70 leg receiving means
72 motor
74 rotating disc
80 camera
90 mirror
92 step motor
95 handling device
96 conveyor
97 loading station
98 unloading station
99 housing
100 sample container
101 lid
200 robot
300 robot
A input storage area
B first intermediate storage area
C second intermediate storage area
D third intermediate storage area
E fourth intermediate storage area
F centrifuge area
G lid removal area
H fifth intermediate storage area
I sixth intermediate storage area
L seventh intermediate storage area
K output storage area
Z central area

The invention claimed is:

1. Method for automatically handling a sample container, comprising the steps of:
    putting at least one sample container in a carrier unit of a container carrier in a handling device, said sample container includes a lid;
    gripping said sample container, using a lifting gripper, from a starting point in said carrier unit and lifting said sample container out of said carrier;
    subsequently, gripping a lid with a gripper head;
    subsequently releasing said grip of said lifting gripper on said sample container;
    subsequently, using said gripper head, rotating said sample container at least 360° while said sample container is gripped by said gripper head;
    after said rotation, again gripping said sample container with said lifting gripper;
    subsequently, removing said lid from said sample container with a combined translational and rotational movement; and,
    bringing said sample container again to said starting position in said carrier unit after removal of said lid.

2. Method according to claim 1, further comprising the steps of:
    by means of an optical capturing device, said lid as well as said sample container are analyzed and are assigned to a lid and sample container type;
    a torque required for removing said lid is assigned to each lid and/or sample container type; and,
    starting from said assigned torque required, a gripping force of said gripper head is adjusted.

3. Method according to claim 1, further comprising the step of:
    an optical capturing device determines whether said lid of said sample container is already removed.

4. Method according to claim 1, further comprising the step of:
    a code applied to said sample container is detected by an optical capturing device during rotation of said sample container.

5. Method according to claim 1, further comprising the steps of:
    a position code optical capturing device for determining said position of said code applied to said sample container, and,
    said sample container is rotated beyond 360° until said code is at a defined position.

6. Method according to claim 1, further comprising the step of:
    controlling the position of said sample container in the carrier unit using an optical capturing device.

7. Method according to claim 1, wherein said lid is colored, further comprising the step of:
    said color of said lid is determined by an optical capturing device; and,
    said lid color is correlated to a lid type related to a processing specification of said sample container.

8. Method according to claim 1, wherein said translational movement is a vertical movement.

9. Method according to claim 1, further comprising the step of putting a plurality of sample containers in said carrier unit.

* * * * *